United States Patent
Emanuele et al.

(10) Patent No.: US 9,714,267 B2
(45) Date of Patent: Jul. 25, 2017

(54) METHOD FOR PROCESSING THIN STILLAGE AND APPARATUS FOR PRODUCING A PROTEIN CONTAINING PRODUCT

(75) Inventors: Mario Emanuele, Oelde (DE); Knud Schöneberg, Stade (DE)

(73) Assignee: GEA Mechanical Equipment GmbH, Oelde (DE)

( * ) Notice: Subject to any disclaimer, the term of this patent is extended or adjusted under 35 U.S.C. 154(b) by 781 days.

(21) Appl. No.: 13/981,559

(22) PCT Filed: Jan. 23, 2012

(86) PCT No.: PCT/EP2012/050940
§ 371 (c)(1),
(2), (4) Date: Jan. 15, 2014

(87) PCT Pub. No.: WO2012/101079
PCT Pub. Date: Aug. 2, 2012

(65) Prior Publication Data
US 2014/0142282 A1    May 22, 2014

(30) Foreign Application Priority Data
Jan. 27, 2011    (EP) .................................... 11152404

(51) Int. Cl.
| | |
|---|---|
| *C07K 1/14* | (2006.01) |
| *C12F 3/10* | (2006.01) |
| *A23J 1/00* | (2006.01) |
| *A23K 1/06* | (2006.01) |

(Continued)

(52) U.S. Cl.
CPC ................ *C07K 1/14* (2013.01); *A23J 1/005* (2013.01); *A23K 10/38* (2016.05); *C12F 3/10* (2013.01); *Y02P 60/873* (2015.11)

(58) Field of Classification Search
CPC ... C07K 1/14; A23K 10/38; C12F 3/10; A23J 1/005; Y02P 60/873
See application file for complete search history.

(56) References Cited

U.S. PATENT DOCUMENTS

| | | |
|---|---|---|
| 4,237,232 A | 12/1980 | Yoshizawa et al. |
| 2004/0082044 A1 | 4/2004 | Prevost et al. |
| 2005/0079270 A1 | 4/2005 | Scheimann |

FOREIGN PATENT DOCUMENTS

| | | |
|---|---|---|
| DE | 3805398 | 8/1989 |
| EP | 0237520 | 9/1987 |
| JP | S57-170150 A | 10/1982 |

(Continued)

OTHER PUBLICATIONS

PCT/EP2012/050940—International Preliminary Report on Patentability and Written Opinion, English translation dated Jul. 30, 2013, 8 pages.

(Continued)

*Primary Examiner* — David A Reifsnyder
(74) *Attorney, Agent, or Firm* — Smith Law Office; Jeffry W. Smith

(57) ABSTRACT

A method for processing thin stillage (TS), characterized by the following steps: a) feeding of thin stillage (TS) into a working vessel (3); b) concentrating of thin stillage (TS) in a filtration unit (9); and c) returning of a first substream of concentrated thin stillage to the thin stillage (TSI) present in the working vessel (3) in order to adjust the solids content, and apparatus for producing a protein-containing product of value.

17 Claims, 2 Drawing Sheets

(51) Int. Cl.
*A23K 1/16* (2006.01)
*A23K 10/38* (2016.01)

(56) References Cited

FOREIGN PATENT DOCUMENTS

| | | |
|---|---|---|
| JP | 06-277455 | 10/1994 |
| JP | 2004-166597 A | 6/2004 |
| JP | 2006-320206 A | 11/2006 |

OTHER PUBLICATIONS

Egg, Richard P. "Grain Sorghum Stillage Recycling: Effect on Ethanol Yield and Stillage Quality" Dec. 1985 Biotechnology and Bioengineering, pp. 1735-1738, vol. 27, John Wiley & Sons, Inc.
PCT/EP2012/050940, International Search Report, dated Feb. 22, 2012.
PCT/EP2012/050940, International Preliminary Report on Patentability and Written Opinion, dated Feb. 22, 2012.

METHOD FOR PROCESSING THIN STILLAGE AND APPARATUS FOR PRODUCING A PROTEIN CONTAINING PRODUCT

FIELD AND BACKGROUND OF THE INVENTION

In the recovery of ethanol in a distillation process, recovered from grains such as corn, wheat and/or triticale, a large amount of stillage is left behind.

This stillage can be used as a feed for livestock farming, among other things.

In the conventional process up until now, the stillage is separated into thin stillage and thick stillage in a decanter. The thin stillage is fed to an evaporator for further reduction in water content and for further concentration. This process step leads to what is known as "stillage syrup". Then, the thick stillage is mixed back in with the stillage syrup and fed to a dryer which takes the dry matter content to above 90 wt.-%. However, this recovered feed can only be fed to ruminants since the fraction of fibrous material is very high, the use of this nutritious feed additive therefore being limited to only a few areas of application.

DE 20 2009 013 389.3 discloses a device for recovering a product in which the thin stillage is concentrated by way of ultrafiltration and then is sent to a dryer together with the thick stillage. This device has essentially proven its effectiveness, but in this case as well, the product produced can only be fed to ruminants. In addition, it has been shown that in the processing of the thin stillage, ultrafiltration can only be operated economically up to a certain concentration level.

SUMMARY OF THE INVENTION

Hence, the object of the present invention on the one hand is to provide a method that ensures optimum operation of a filtration unit, and on the other hand provides a device for manufacturing a product of value that contains proteins and fats, and is essentially free of fiber.

According to the invention, a method for processing thin stillage comprises the following steps:
  a) Feeding of thin stillage into a working vessel;
  b) Filtering and pre-concentrating thin stillage in a filtration unit; and
  c) Returning a first substream of pre-concentrated thin stillage to the thin stillage contained in the working vessel in order to adjust the amount of dry matter.

By returning the first substream of pre-concentrated thin stillage to the thin stillage located in the working vessel, the dry matter content of the thin stillage can be raised, which facilitates a more optimal process and a higher efficiency of the filtration unit.

After the pre-concentration of the thin stillage by way of the filtration unit, the flow can be split, wherein a first substream is returned to the working vessel and a second substream is further processed.

After the filtration unit, this second substream can be routed to a mechanical solid-liquid separator in which the thin stillage is further concentrated to advantageously form a thin stillage with a dry matter content of preferably greater than 12 wt.-%. By combining a filtration unit with a centrifuge, the thin stillage can be advantageously concentrated in a particularly temperature-sensitive manner.

After further concentration of the thin stillage by way of clarification and decanting of the clarified aqueous phase, the centrifuged thin stillage is transferred as a separator nozzle phase to a dryer, for example a spray dryer, where a product of value containing protein and that is essentially free of fiber is formed by way of drying the concentrated thin stillage, the product being suitable as a feed additive, for example.

The drying can be done in a product-sensitive manner, in other words with no drying in furnaces, flames or the like such that the valuable contents are not damaged by the effect of heat. However, drying can also be done after processing in the centrifuge.

It is advantageous that the thin stillage fed to the working vessel can be prepared by processing grain stillage in a decanter, for example following a distillation process.

It is further advantageous if in addition to the concentrated thin stillage a permeate stream is discharged from the filtration unit, the permeate stream optionally being routable to an anaerobic wastewater treatment facility, for example, or being reusable as process water. This is advantageous since the wastewater can be easily processed as a result and a separate collection and storage system can be avoided, as is frequently needed in this case for process wastewater.

According to the invention, a device for producing a valuable product containing protein from thin stillage comprises a working vessel, a filtration unit, a centrifuge, preferably a separator and a dryer, wherein the filtration unit is connected to the working vessel by way of a return line for a first substream of the concentrated thin stillage. This operating mode results in a nearly fiber-free valuable product, with the filtration unit operating efficiently.

The invention is explained in more detail through the following exemplary embodiment and with the aid of the drawings in FIGS. 1 and 2. Shown are:

DETAILED DESCRIPTION OF THE INVENTION

Figure 2:
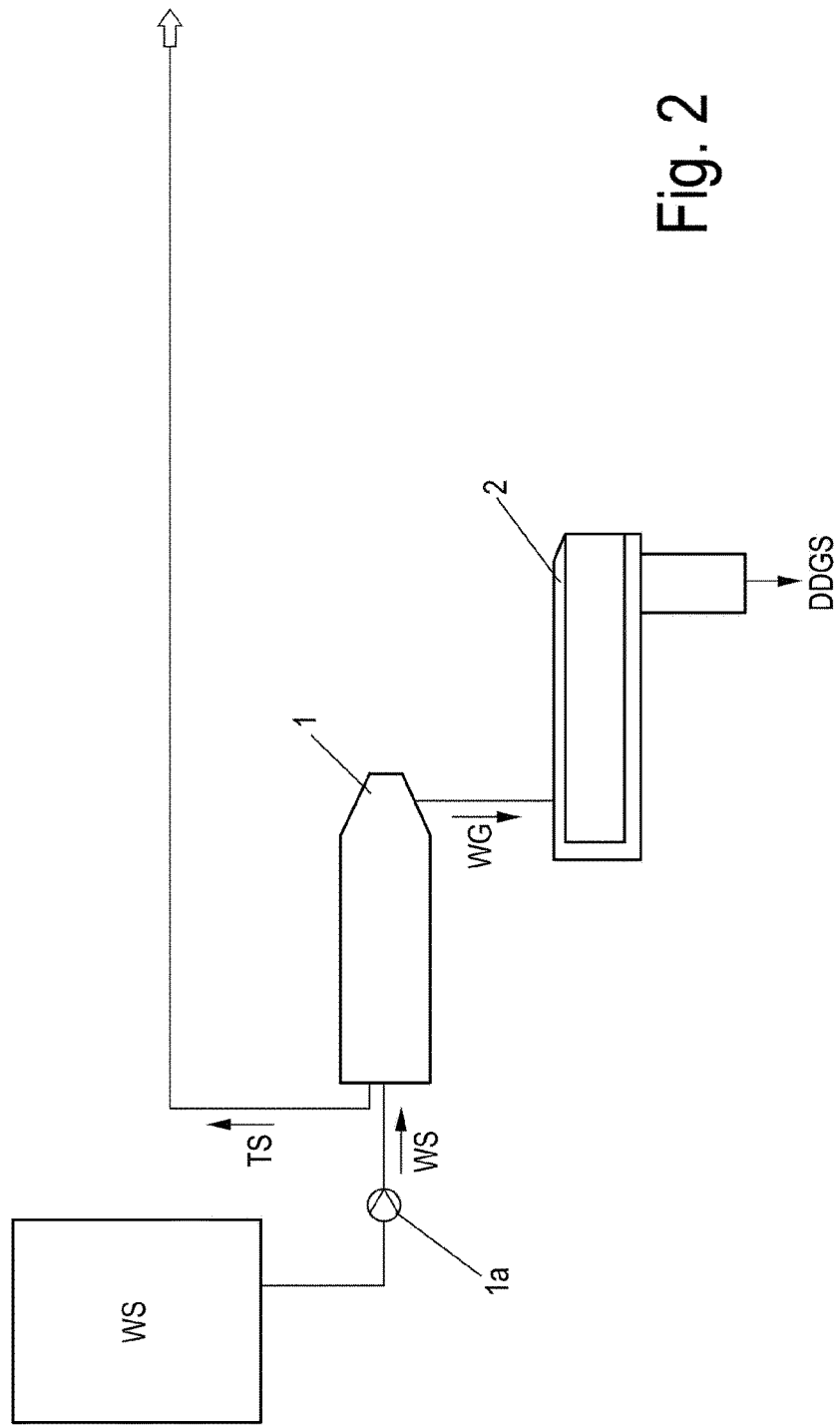

FIG. 2 shows a known processing step for a grain stillage (whole stillage) WS, for example following an ethanol distillation process. This stillage WS has a dry matter content of about 10 wt.-%, with about 7 wt.-% being suspended solids and 3 wt.-% being dissolved solids, and is routed through a pump 1a to a decanter 1 where the stillage is processed into thick stillage (wet grains) WG and thin stillage TS.

The fraction of dry matter in the thin stillage TS is about 4.15 wt.-% relative to the total mass of thin stillage TS, with about 1.15 wt.-% being suspended solids and about 3 wt.-% being dissolved solids. The fraction of dry matter in the wet grains WG is greater than 30 wt.-% relative to the total mass of the wet grains WG.

The wet grains are routed from the decanter 1 to a dryer, such as a drum dryer 2, where the carrier fluid of the wet grains, usually water, is evaporated as much as possible resulting in a nutritious solid, called dry stillage (dried distillers grains with solubles) DDGS, which is used as a feed for livestock farming, among other things.

The thin stillage has a volumetric flow of 6-7 m3/h and is then forwarded to a working vessel 3. (FIG. 2.)

Figure 1:
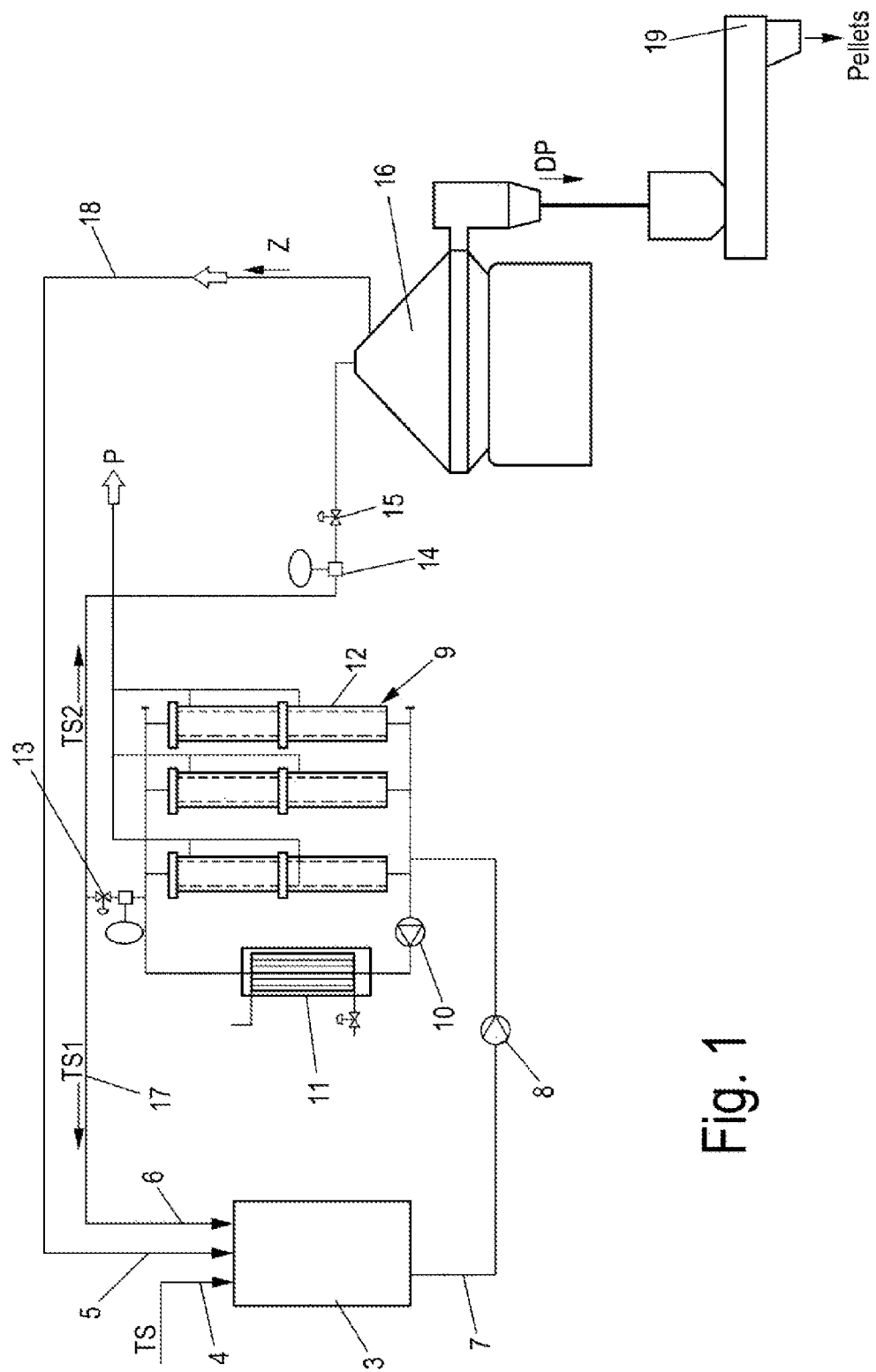
FIG. 1 A schematic representation of a device for manufacturing a valuable product from thin stillage and FIG. 2 A schematic representation of a known process for preparing thin stillage.

The recovery of proteins and fats from thin stillage TS is described in more detail using a concrete exemplary embodiment in the system of FIG. 1.

The working vessel 3 holds 20 m³ in this concrete exemplary embodiment, and has a total of three inputs 4, 5 and 6. Input 4 of the working vessel 3 is an input for feeding thin stillage (TS) to the system, the input fed from the decanter 1 in FIG. 2, for example. The other inputs 5 and 6 to the working vessel 3 are provided for recycled thin stillage from the process and for the supernatant liquid phase.

The working vessel 3 also comprises an outlet 7 that connects the working vessel 3 to an ultrafiltration unit 9 and allows the transfer of thin stillage from the working vessel 3 to the ultrafiltration unit 9. The thin stillage is transported from the working vessel 3 to the ultrafiltration unit 9 by way of a feed pump 8 at a pressure of 3-4 bar, wherein the feed pump power output is preferably 15 KW.

The ultrafiltration unit 9 is only shown schematically in FIG. 1 and comprises at least one loop pump 10, a cooler 11 and one or more ultrafiltration modules 12.

During the filtration, liquid is drawn out of the thin stillage and is discharged from the ultrafiltration unit 9 as permeate P at a volumetric flow of about 6 m³/h.

A plurality of ceramic membrane filter rods (not shown), preferably alpha-aluminum oxide and zirconium oxide filter rods, are disposed in the ultrafiltration modules 12. These membrane filter rods are penetrated by parallel channels running in the longitudinal direction thereof, wherein the channels comprise a filter membrane, consisting of zirconium oxide deposited on an alpha-aluminum oxide carrier substance, along the channel wall and the entire perimeter thereof. In the process, the zirconium oxide layer comprises finely distributed pores, whereas the support material is constructed of aluminum oxide with coarse pores. The filter membrane has an average pore size of 50 nm.

A total of 168 membrane filter rods are disposed in the six ultrafiltration modules shown in FIG. 2. These filter rods provide a filtering surface area of 72 m² for separating liquid from the thin stillage. In the process, the permeate is forced through the ceramic filter membrane by the 3-4 bar of pressure produced by the feed pump. The retentate and the pre-concentrated thin stillage are discharged from the ultra-filtration unit by way of a control valve 13.

Solids that are not able to pass through the 50 nm pores of the filter membrane build up on the surface of the membrane during filtration. In order to prevent plugging of the filter membrane, a turbulent flow of 5 m/s can be generated by the loop pump 10 with the valve 13 closed, at a volumetric flow of 810 m³/h. Such a flow can loosen or remove the accumulated solid particles from the filter membrane.

After filtration, a concentrated thin stillage leaves the ultrafiltration unit as a retentate and is divided into two substreams TS1 and TS2.

A second retentate substream or concentrated thin stillage substream TS2, which is preferably about 4-5 m³/h, is sent to a centrifuge, preferably a two-phase separator 16. The extent of the substream can be controlled by means for splitting flow, in this case a valve 15, for example as a function of the flow rate. This flow rate can be determined through a sensor 14 which then adjusts the flow to a pre-determined setpoint by way of the valve 15.

In the centrifuge, the retentate produced in the ultrafiltration process is concentrated to a dry matter content of preferably greater than 12 wt.-%, wherein a clarified liquid is discharged at the overflow of the centrifuge as a supernatant liquid Z.

The supernatant liquid Z has a solids fraction of less than one vol.-% and is returned from the centrifuge 16 to the working vessel through the return line 18 and the input 5 at a volumetric flow rate of 2.2-3.2 m³/h. The nozzle phase DP or centrifuged phase has a dry matter content of more than 12 wt.-%, preferably up to 18 wt.-% and an FC factor of 7-8, and is then processed into a transportable and storable product using a dryer, not shown here. This product can be converted to a more compact form, such as pellets, for example using a pelleting press 19. The pellets thus produced can be used as valuable feed additives, and have a fraction of dry matter of over 90 wt.-%, of which 40% is protein, 55% is fat and the rest is fiber and ash.

A fractional second flow substream TS1 of 30 m/h is returned to the working vessel 3 through a return line 17 and the input 6 by way of flow control and mixed with the thin stillage from the decanter of the input 4 so that a dry matter content of about 7 wt.-% is adjusted for the thin stillage in the working vessel 3 and the FC factor, a concentration factor, is raised by a factor of 3 to 4 compared to the thin stillage from the decanter 1.

The thin stillage TS leaving the decanter 1 is concentrated by the return line 17 for returning or recycling a second retentate substream TS2 to the working vessel 3. It was surprising to find that the optimum operating point for an ultrafiltration unit 9 in the processing of thin stillage is reached at a concentration of thin stillage TS to a dry matter content of about 7%.

Solid particles in the size range of 5-100 nm were removed from the permeate P separated from the ultrafiltration unit 9, the permeate volume being preferably 6 m³/h and primarily water, so that this permeate can be fed to the community wastewater treatment facility or can be subjected to an anaerobic wastewater treatment. Moreover, the aqueous phase could be further used as process water, for example for creating a mash.

The invention claimed is:

1. A method for processing thin stillage, comprising the steps of:
   a) feeding thin stillage into a working vessel;
   b) concentrating the thin stillage in a filtration unit;
   c) returning a first substream of concentrated thin stillage to the thin stillage contained in the working vessel to adjust the amount of dry matter content of the thin stillage in the working vessel;
   d) concentrating the thin stillage in the filtration unit, and
   e) splitting a flow of the concentrated thin stillage into the first substream and a second substream.

2. The method as claimed in claim 1, and further comprising the step of:
   clarifying at least the second substream of the concentrated thin stillage in a centrifuge to further concentrate the thin stillage.

3. The method as claimed in claim 2, wherein the further concentrated thin stillage has a dry matter amount of more than 12 percent by weight.

4. The method of claim 2, and further comprising the steps of:
   drying the concentrated thin stillage; and
   forming therefrom a protein containing product.

5. The method of claim 2, wherein the further concentrated thin stillage has a dry matter amount of more than 18 percent by weight.

6. The method of claim 1, wherein the first substream is at least three times greater than a second substream of concentrated thin stillage.

7. The method of claim 1, and further comprising the step of:
processing grain stillage in a decanter to obtain the thin stillage.

8. The method of claim 1, and further comprising the steps of:
discharging a permeate stream from the filtration unit; and
routing the permeate stream to an anaerobic wastewater treatment facility.

9. The method of claim 1, wherein the step of concentrating the thin stillage in a filtration unit is controlled as a function of the dry matter content of the thin stillage located in the working vessel.

10. The method of claim 1, and further comprising the step of:
controlling thin stillage flow based on a thin stillage flow rate after concentration of thin stillage in a filtration unit.

11. The method of claim 1, and further comprising the step of:
clarifying at least the second substream of the concentrated thin stillage in a separator to further concentrate the thin stillage.

12. The method of claim 1, wherein the first substream is at least six times greater than a second substream of concentrated thin stillage.

13. The method of claim 1, and further comprising the steps of:
discharging a permeate stream from the filtration unit, and reusing the permeate stream as process water.

14. A device for producing a product containing protein from thin stillage, the device comprising:
a working vessel;
a thin stillage concentrating filtration unit in fluid communication with the working vessel and the thin stillage concentrating filtration unit includes:
a flow splitter in which concentrated stillage is split into a first substream and a second substream;
a centrifuge in fluid communication with the thin stillage concentrating filtration unit;
a dryer in fluid communication with the centrifuge; and
a return line between the flow splitter and the working vessel for returning the first substream of concentrated thin stillage to the working vessel.

15. The device of claim 14, wherein the thin stillage concentrating filtration unit is an ultrafiltration unit.

16. The device of claim 14, and
wherein the flow splitter in which the concentrated stillage is split into a first substream and a second substream, and is regulated as a function of the flow rate.

17. The device of claim 14, wherein the centrifuge is connected to the working vessel by way of a return line for returning a clarified centrifugate phase to the working vessel.

* * * * *